(12) United States Patent
Hawkins et al.

(10) Patent No.: US 7,294,129 B2
(45) Date of Patent: Nov. 13, 2007

(54) SPINAL FIXATION DEVICE AND ASSOCIATED METHOD

(75) Inventors: Nathaniel E Hawkins, Lake Hiawatha, NJ (US); Stephen Esses, Houston, TX (US); Kirk J Bailey, Blairstown, NJ (US); Rui J Ferreira, Livingston, NJ (US)

(73) Assignee: EBI, L.P., Parsippany, NJ (US)

( * ) Notice: Subject to any disclaimer, the term of this patent is extended or adjusted under 35 U.S.C. 154(b) by 278 days.

(21) Appl. No.: 11/062,330

(22) Filed: Feb. 18, 2005

(65) Prior Publication Data

US 2006/0200130 A1 Sep. 7, 2006

(51) Int. Cl.
*A61F 2/30* (2006.01)
(52) U.S. Cl. .......................................... 606/61
(58) Field of Classification Search ................ 606/53, 606/96, 61, 72–73; 623/17.11
See application file for complete search history.

(56) References Cited

U.S. PATENT DOCUMENTS

| | | | |
|---|---|---|---|
| 5,334,203 A * | 8/1994 | Wagner | 606/61 |
| 5,375,823 A | 12/1994 | Navas | |
| 5,437,669 A * | 8/1995 | Yuan et al. | 606/61 |
| 5,645,599 A | 7/1997 | Samani | |
| 5,733,284 A | 3/1998 | Martin | |
| 6,241,730 B1 | 6/2001 | Alby | |
| 6,267,764 B1 | 7/2001 | Elberg | |
| 6,293,949 B1 | 9/2001 | Justis et al. | |
| 6,402,750 B1 | 6/2002 | Atkinson et al. | |
| 6,419,703 B1 | 7/2002 | Fallin et al. | |
| 6,440,169 B1 | 8/2002 | Elberg et al. | |
| 6,626,904 B1 | 9/2003 | Jammet et al. | |
| 6,669,729 B2 | 12/2003 | Chin | |
| 2002/0035366 A1 | 3/2002 | Walder et al. | |
| 2002/0052603 A1 * | 5/2002 | Nichols et al. | 606/61 |
| 2002/0143330 A1 * | 10/2002 | Shluzas | 606/61 |
| 2003/0191470 A1 | 10/2003 | Ritland | |
| 2003/0220643 A1 | 11/2003 | Ferree | |
| 2004/0002708 A1 | 1/2004 | Ritland | |
| 2004/0049190 A1 | 3/2004 | Biedermann et al. | |
| 2004/0073215 A1 | 4/2004 | Carli | |
| 2005/0033295 A1 * | 2/2005 | Wisnewski | 606/61 |
| 2005/0080420 A1 * | 4/2005 | Farris et al. | 606/61 |

FOREIGN PATENT DOCUMENTS

| | | |
|---|---|---|
| DE | 28 45 647 | 5/1980 |
| FR | 2709245 | 3/1995 |
| WO | WO 01/39678 | 6/2001 |
| WO | WO 2004/098452 | 11/2004 |

* cited by examiner

*Primary Examiner*—Eduardo C. Robert
*Assistant Examiner*—Anitza M San Miguel
(74) *Attorney, Agent, or Firm*—Harness, Dickey & Pierce, P.L.C.

(57) ABSTRACT

A spinal fixation device. The spinal fixation device includes a plurality of arm assemblies. Each arm assembly can be attached to a single vertebra. Pairs of adjacent arm assemblies can be movably coupled to one another by one or more telescopic assemblies. The telescopic assemblies can oriented substantially transversely to the vertebrae and allow relative movement between the vertebrae.

28 Claims, 11 Drawing Sheets

SPINAL FIXATION DEVICE AND ASSOCIATED METHOD

Several implant designs for the posterior region of the spine are known. Some of the known implants provide dynamic motion between adjacent vertebrae using, for example, hinged articulation members, deformable links, springs, and the like. Retaining some dynamic motion is desirable in particular after spinal surgery has been performed, such as laminectomy, facetectomy, or total decompression.

Although the known implants are satisfactory for their purposes, there is still a need for spinal fixation devices for the posterior spine that provide dynamic motion, and yet limit the amount of compression of the posterior vertebrae.

SUMMARY

The present teachings provide a spinal fixation device comprising first and second arm assemblies for attachment to first and second vertebrae, and at least one telescopic assembly interconnecting the first and second arm assemblies for relative motion therebetween.

In one aspect, the present teachings provide a spinal fixation device comprising a plurality of arm assemblies attachable to corresponding vertebrae. The plurality of arm assemblies are interconnected with one or more telescopic assemblies for relative movement therebetween.

The present teachings also provide a method for spinal fixation. The method includes providing a spinal fixation device having first and second arm assemblies interconnected with one or more telescopic assemblies for relative movement therebetween, constraining the spinal fixation device with an assembly holder, inserting a pair of pedicle fasteners on each of first and second adjacent vertebrae, coupling the spinal fixation device to the pedicle fasteners, and removing the assembly holder.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses. For example, although the present teachings are illustrated for posterior spine fixation, the present teachings can be used for fixation of other bones. Further, although the present teachings are illustrated for fixation between two vertebrae (two-tier fixation), additional consecutive vertebrae can be interconnected by the same fixation device (multi-tier fixation).

Figure 1:
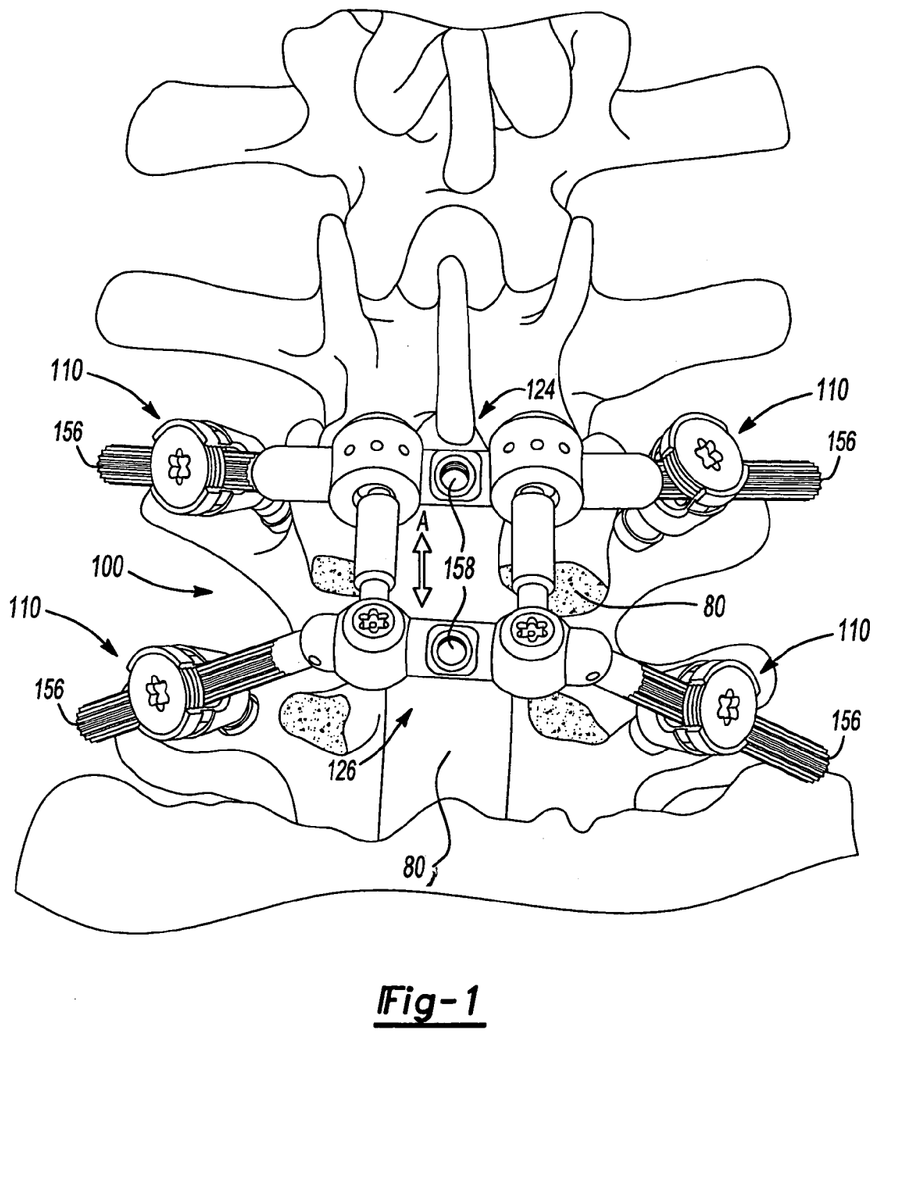
FIG. 1 is a perspective view of a spinal fixation device according to the present teachings, the spinal fixation device shown coupled to two vertebrae.
Figure 2:
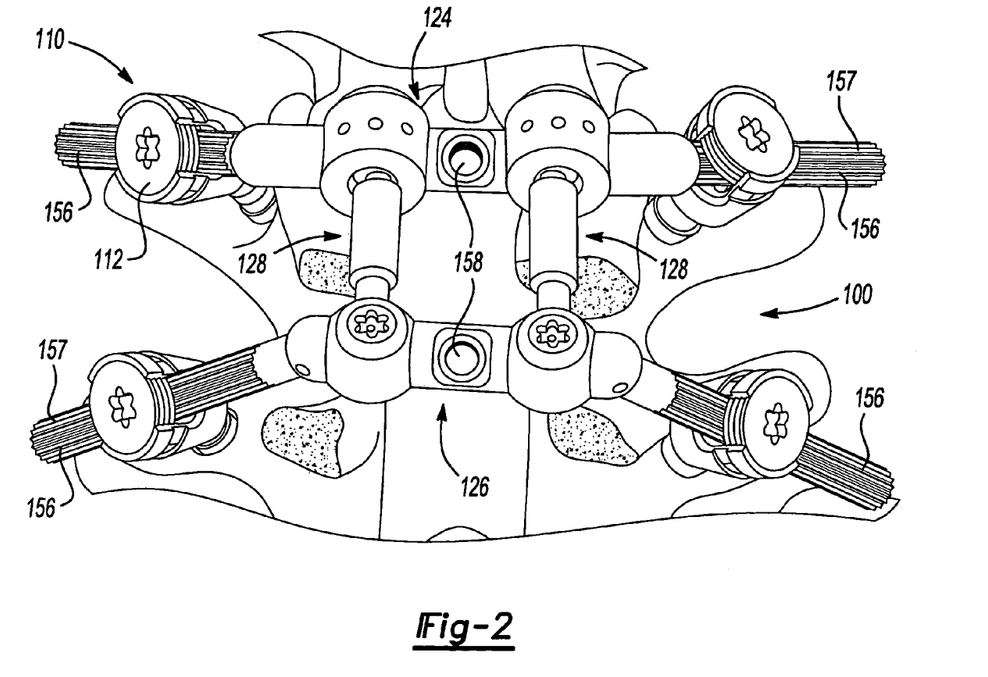
FIG. 2 is an enlarged view of the spinal fixation device of FIG. 1.
Figure 3:
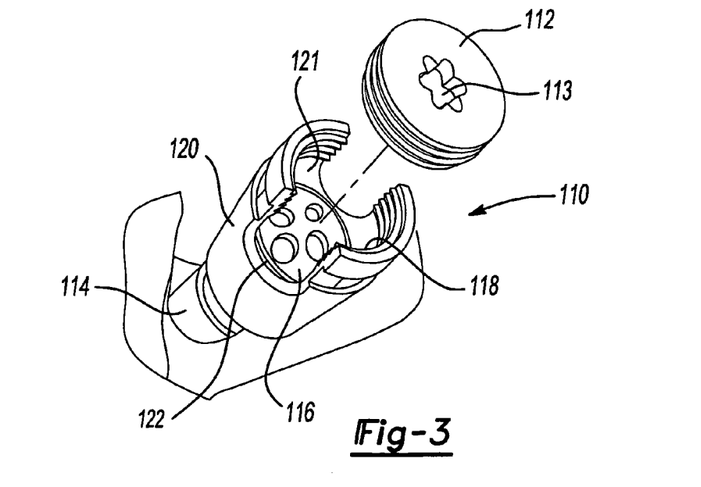
FIG. 3 is a partially exploded view of a pedicle fastener for use with the spinal fixation device of FIG. 1.

Referring to FIGS. 1-3, an exemplary two-tier spinal fixation device 100 according to the present teachings is illustrated attached to two vertebrae 80 of the posterior spine. As shown, the spinal fixation device 100 may be attached to the pedicles of the two vertebrae 80 with multidirectional pedicle fasteners 110. The pedicle fasteners 110 can be of the type disclosed in commonly assigned U.S. Pat. No. 6,599,290, which is incorporated by reference herein in its entirety. Each pedicle fastener 110, for example, can include an anchoring shaft 114 terminating in a ball 116 that is received in a socket 118 of an adapter 120 and secured therein with a split ring 122. The adapter 120 provides a receptacle 121 for receiving a corresponding arm 156 of the spinal fixation device 100. The ball and socket connection of the pedicle fastener 110 enables 360° rotation of the shaft 114 about its longitudinal axis as well as multidirectional orientation (angulation) of the shaft 114 relative to the adapter 120. A set screw 112 having tool engagement formations 113 and a threaded portion 115 can be used to secure the arm 156 of the spinal fixation device 100 to the pedicle fasteners 110, as discussed herein below. The threaded portion 115 of the set screw 112 engages complementary threads 117 of the interior surface of the receptacle 121. It will be appreciated that other multidirectional, semi-constrained or fully constrained pedicle fasteners 110 can be also used with the spinal fixation device 100.

Referring to FIGS. 2, and 4-6, the spinal fixation device 100 can include first and second arm assemblies 124, 126 for two-tier fixation or three or more arm assemblies for multi-tier fixation. For clarity, the following description is directed to two-tier fixation, although the invention will be understood to be equally applicable to multi-tier fixation. The first and second arm assemblies 124, 126 can be movably coupled to each other with one or more telescopic assemblies 128, shown in exploded view in FIG. 4. Each telescopic assembly 128 can include first and second shafts 130, 132, which are configured for telescopic and slidable coupling therebetween for providing relative movement between the first and second arm assemblies 124, 126 in the direction of the double arrow A (see FIG. 1). One of the first and second shafts 130, 132 can have, for example, a longitudinal bore 134 for slidably receiving the other of the first and second shafts 130, 132. The telescopic connection between the first and second shafts 130, 132 allows dynamic motion of the spine, while limiting compression to an amount that can be predetermined and controlled by selecting the appropriate size and length for the telescopic assembly 128. Although the shafts 130, 132 are illustrated as rods with circular cross-sections, bars with oval, rectangular or other cross-sectional shapes can also be used. In one aspect, the first shaft 130 can terminate in a ball head or other convex projection 136, and the second shaft 132 can terminate in a flattened or planar head 138. The flattened head 138 can have concave recesses 140, such as semi-spherical recesses, on opposing sides.

Figures 4, 4A:
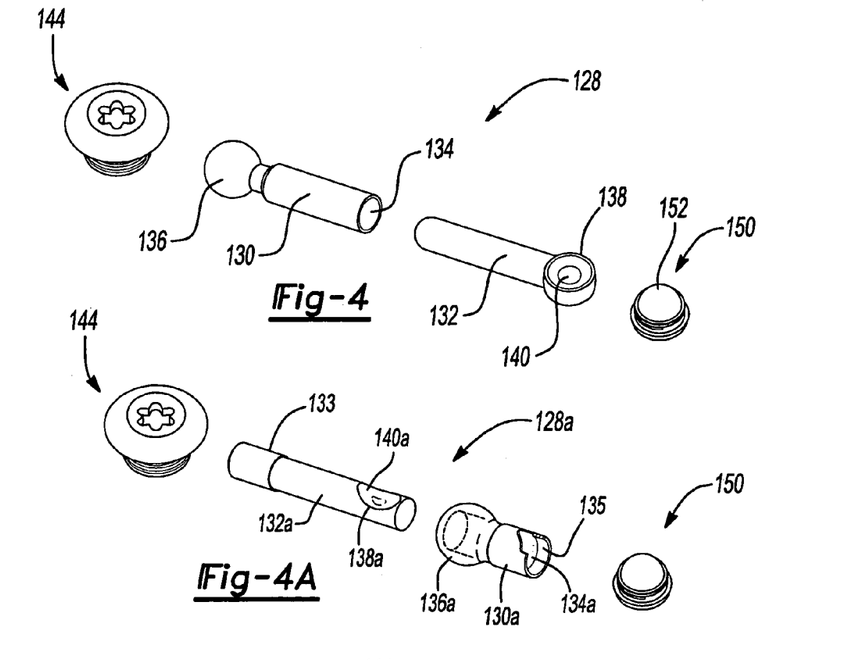
FIG. 4 is an exploded view of a telescoping assembly of the spinal fixation device of FIG. 2.
FIG. 4A is an exploded view of a telescoping assembly of a spinal fixation device according to the present teachings.
Figure 5:
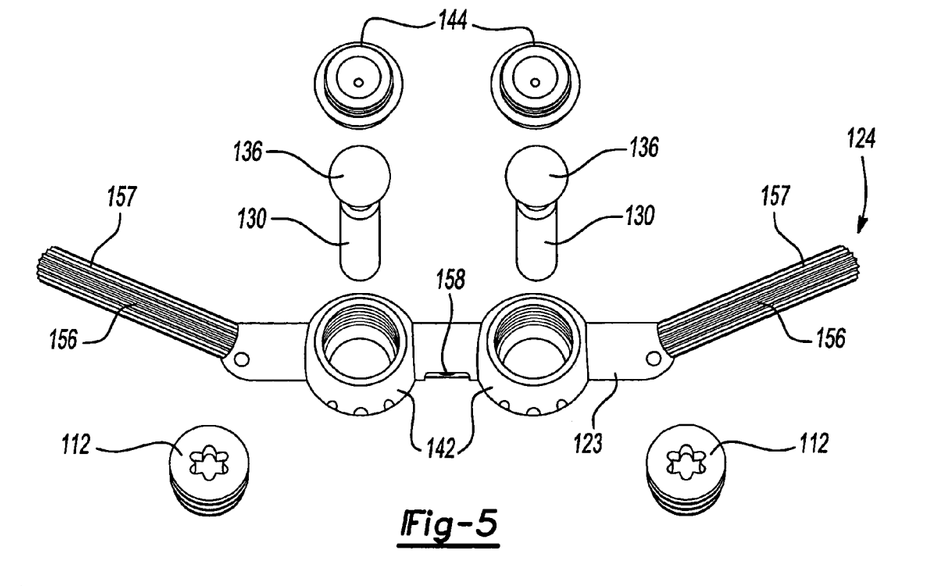
FIG. 5 is a top view of a first arm assembly of the spinal fixation device of FIG. 2.

Each convex projection 136 is configured to be rotatably received in a corresponding spherical or curved ring 142 formed in the first arm assembly 124, and is secured therein with a complementary set screw 144 that can be threadably connected to the curved ring 142. When connected in this manner, the shaft 130 is coupled to the first arm assembly 124 with a ball and socket connection that permits 360° rotational motion and multidirectional three-dimensional orientation (angulation) of the first shaft 130 relative to the first arm assembly 124.

The flattened heads 138 are configured to be received in corresponding openings 148 of spherical or curved shells 146, which are formed in the second arm assembly 126. Each flattened head 138 is secured to the corresponding curved shell 146 with a complementary set screw 150. The set screw 150 can have a convex projection 152 that is configured for coupling with the concave recess 140 of the flattened head 138. When thus connected, the second shaft 132 can angulate in a plane defined by the flattened head 138.

In another aspect of the present teachings, the first and second arm assemblies 124, 126 can be movably coupled to each other with one or more telescopic assemblies 128a, shown in exploded view in FIG. 4A. The telescopic assembly 128a is similar to the telescopic assembly illustrated in FIG. 4A. Similar elements are referenced with similar numbers followed by "a" as in 128, 128a and their description is not repeated in detail. The telescopic assembly 128a can also include first and second shafts 130a, 132a, which are configured for telescopic and slidable coupling therebetween for providing relative movement between the first and second arm assemblies 124, 126. One of the first and second shafts 130a 132a can have, for example, a longitudinal bore 134a for slidably receiving the other of the first and second shafts 130a, 132a. Further, the first and second shafts 130a, 132a can include engagement formations 133, 135, such as, for example, complementary ledges, which prevent complete disengagement of the first and second shafts 130a, 132a. The telescopic connection between the first and second shafts 130a, 132b allows dynamic motion (extension) of the spine to a maximum predetermined amount, while limiting compression to another predetermined amount. The possible amounts of extension and compression can be controlled by selecting the appropriate size and length for the telescopic assembly 128a.

Figures 6, 7:
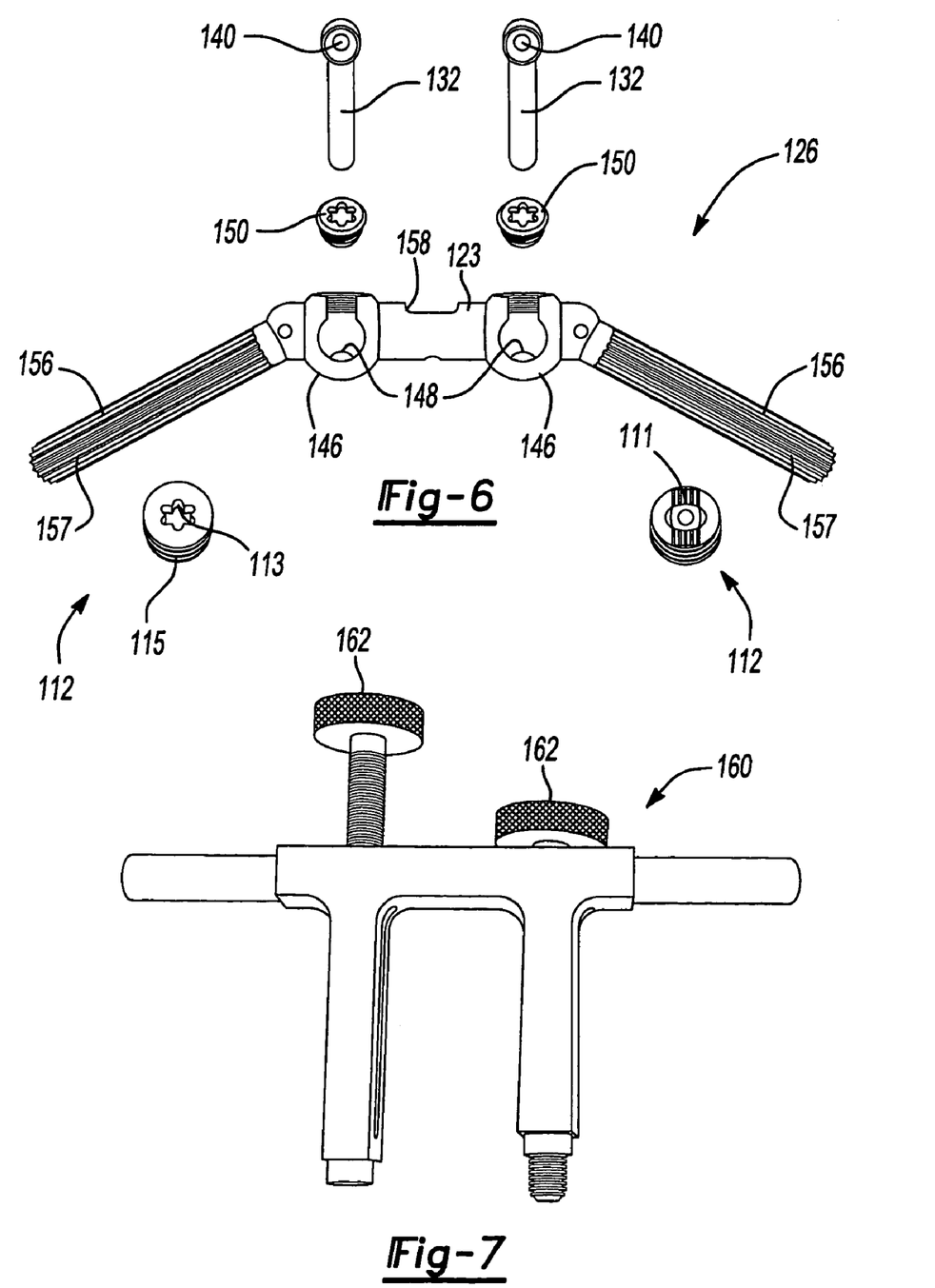
FIG. 6 is a top view of a second arm assembly of the spinal fixation device of FIG. 2.
FIG. 7 is a side view of an assembly holder for the spinal fixation device of FIG. 2.
Figure 7A:
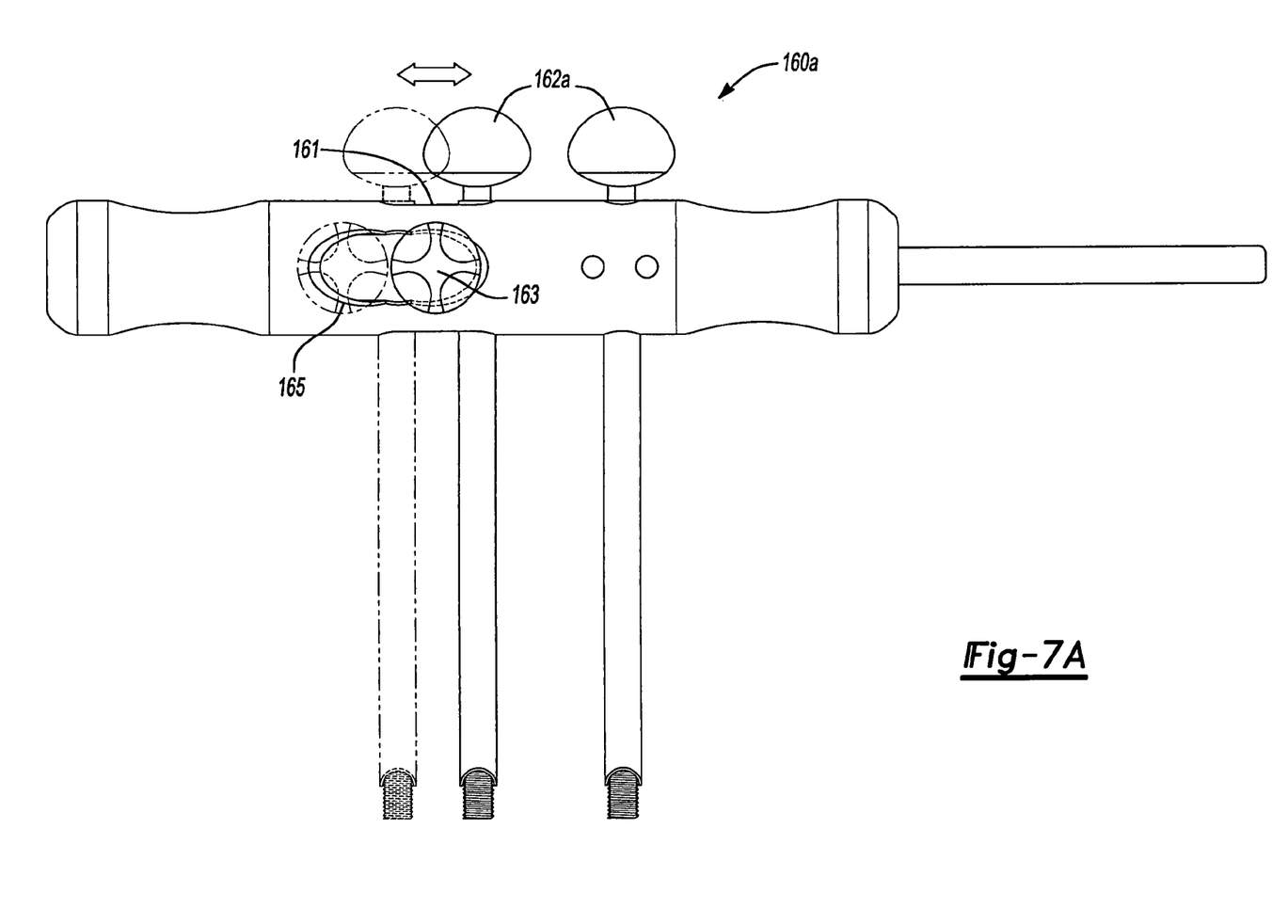
FIG. 7A is a side view of an assembly holder for a spinal fixation device according to the present teachings.
Figure 10:
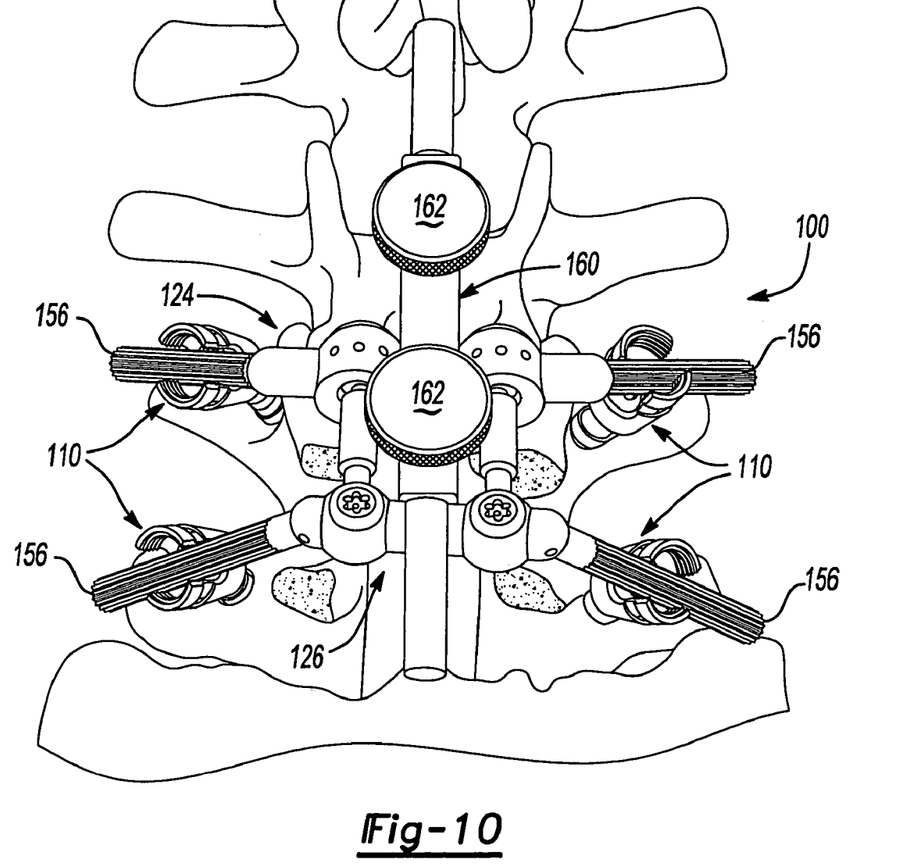

Referring to FIGS. 2, 7, 7A and 10, each arm assembly 124, 126 can include a central portion 123 and pair of arms 156 extending therefrom for attachment to the pedicle fasteners 110. The arm assemblies 124, 126 provide a structure for securing the spinal fixation device 100 to the pedicles of the vertebrae 80. The arms 156 can be angled relative to the central portion 123 for better structural conformance to the pedicles of the vertebrae. Further, each arm assembly 124, 126 can include an opening 158 for receiving a corresponding fastener 162 of a temporary assembly holder 160, 160a, as illustrated in FIGS. 10, 7 and 7A and described below.

Figure 8:
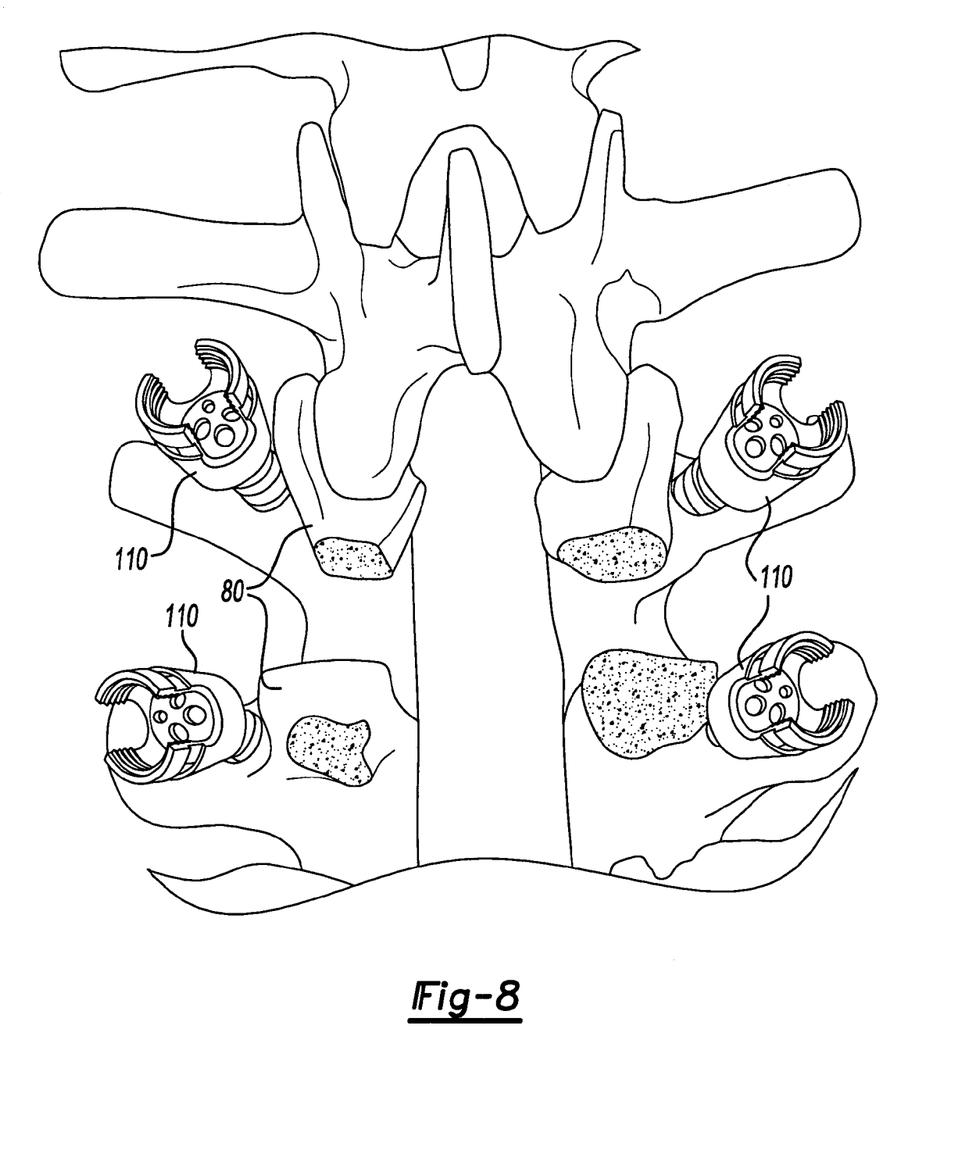
FIGS. 8-13 illustrate progressive implantation stages of the spinal fixation device of FIG. 1.
Figure 9:
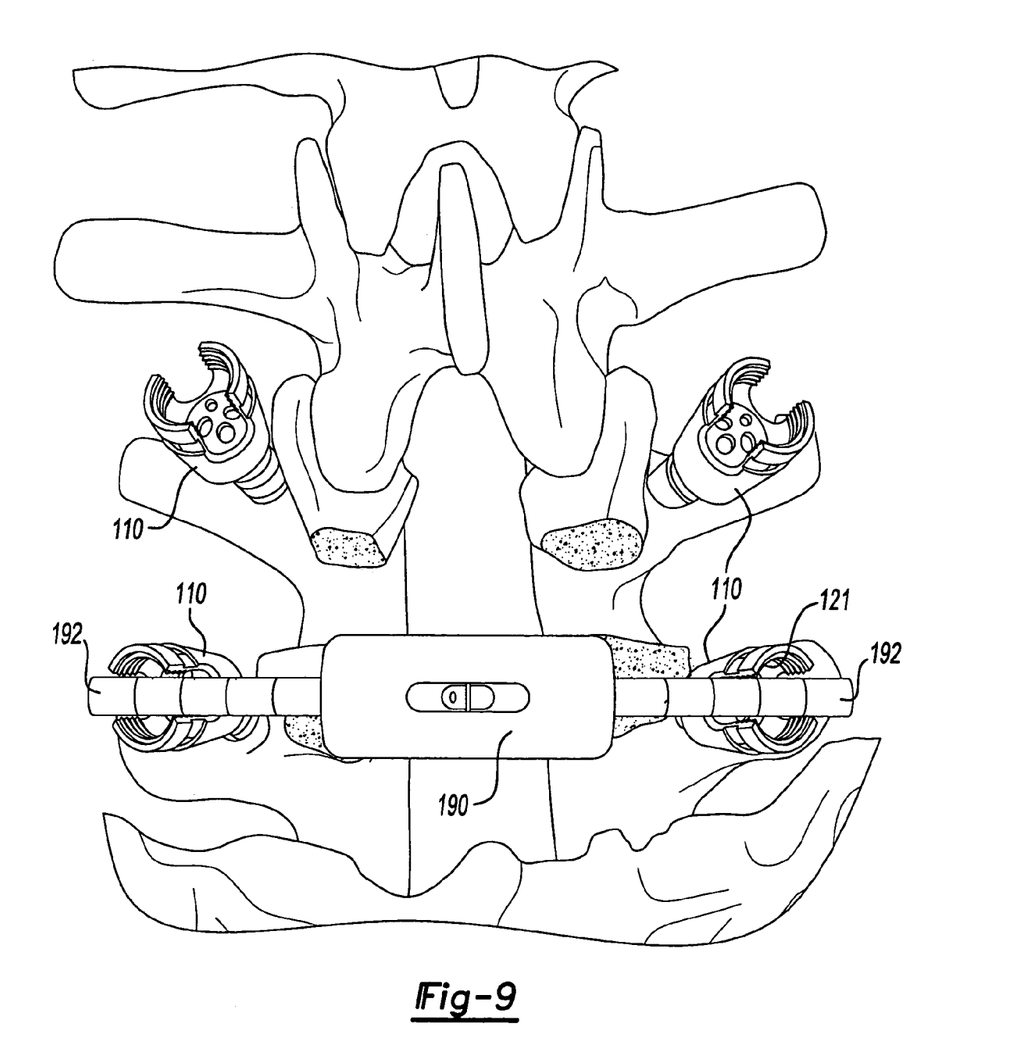

Referring to FIGS. 8-13, an exemplary implantation procedure of the spinal fixation device 100 is illustrated. The multidirectional pedicle fasteners 110 are first implanted in pairs into the pedicles of each vertebra 80, as shown in FIG. 8. Each pair of pedicle fasteners 110 can be leveled horizontally (transversely to the spinal axis), using a leveler 190 having rods 192. Each rod 192 is configured to be received in the receptacle 121 of the adapter 120, as illustrated in FIG. 9. Vertical leveling (parallel to the spinal axis) is not necessary, in this procedure. At this stage, the distance between the pedicle fasteners 110 in the direction of the spine can also be measured for determining the best size of the spinal fixation device 100.

Referring particularly to FIG. 10, the spinal fixation device 100 can be pre-assembled and stabilized using one of the assembly holders 160, 160a. The fasteners 162, 162a of the corresponding assembly holder 160, 160a are inserted into the openings 158 of the first and second arm assemblies 124, 126 to secure the spinal fixation device 100 in the assembled position during the procedure. Referring to FIG. 7A, one of the fasteners 162a of the assembly holder 160a can be slidably moved in an elongated slot 161 to allow adjustment of the distance between the first and second arm assemblies 124, 126. A set screw 163 movable in a side slot 165 can be used to secure the movable fastener 162a in the slot 161. In this assembled and constrained configuration, the arms 156 of the spinal fixation device 100 are inserted into the receptacles 121 of the pedicle fasteners 110.

Figure 11:
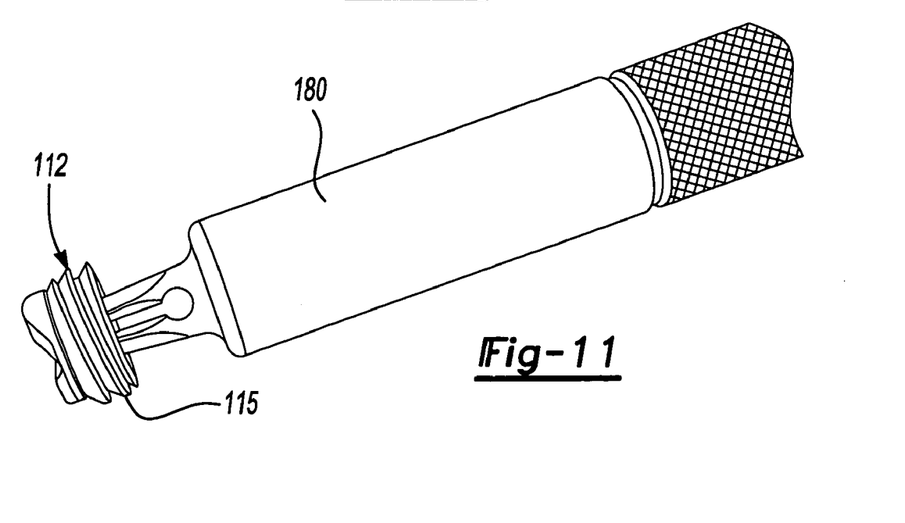
Figure 12:
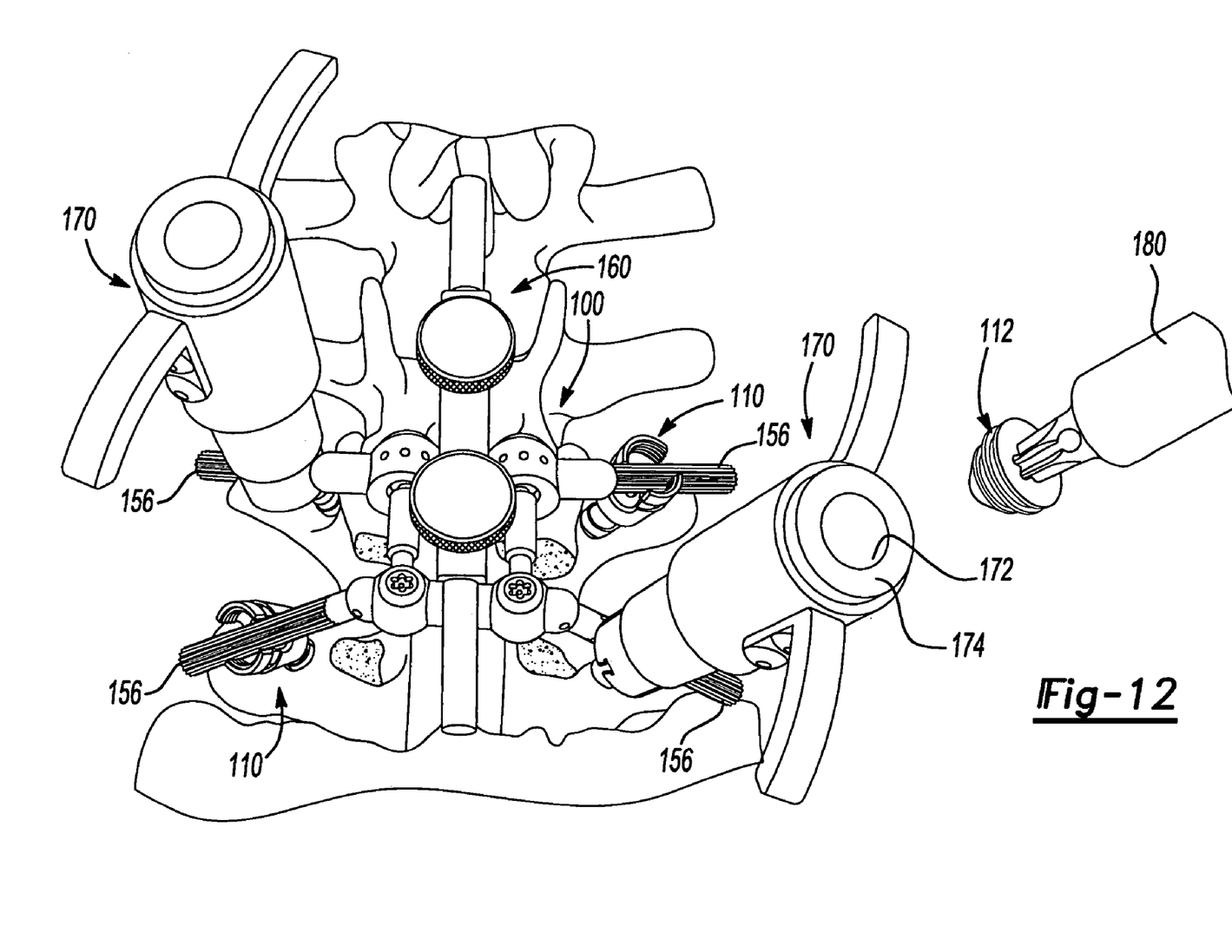

Referring to FIGS. 11 and 12, the set screws 112 can be inserted over the arms 156 of the spinal fixation device 100 using a guide 170 over each pedicle fastener 110 to hold the spinal fixation device 100 in the implantation position. In one aspect, the guide 170 can include a spring-loaded rod or bar 174 having a bore 172. The guide can also include an O-ring at one end. The O-ring holds the pedicle fastener 110, while the spring-loaded bar 174 pushes against the arm 156 of the spinal fixation device 100. The set screw 112 can then be inserted into the bore 172 with a tool 180 that grips and holds the set screw 112 by the engagement formations 113. The set screw 112 and the arm 156 can have complementary surface engagement formations, such as set screw ridge formations 111, shown on the set screw in FIG. 6, and arm ridge formations 157, shown on the arms 156 in FIG. 2, for better gripping. The threaded portion 115 of the set screw 112 can be engaged with the threads 117 of the adapter 120, although other known engagement methods can be used.

Figure 13:
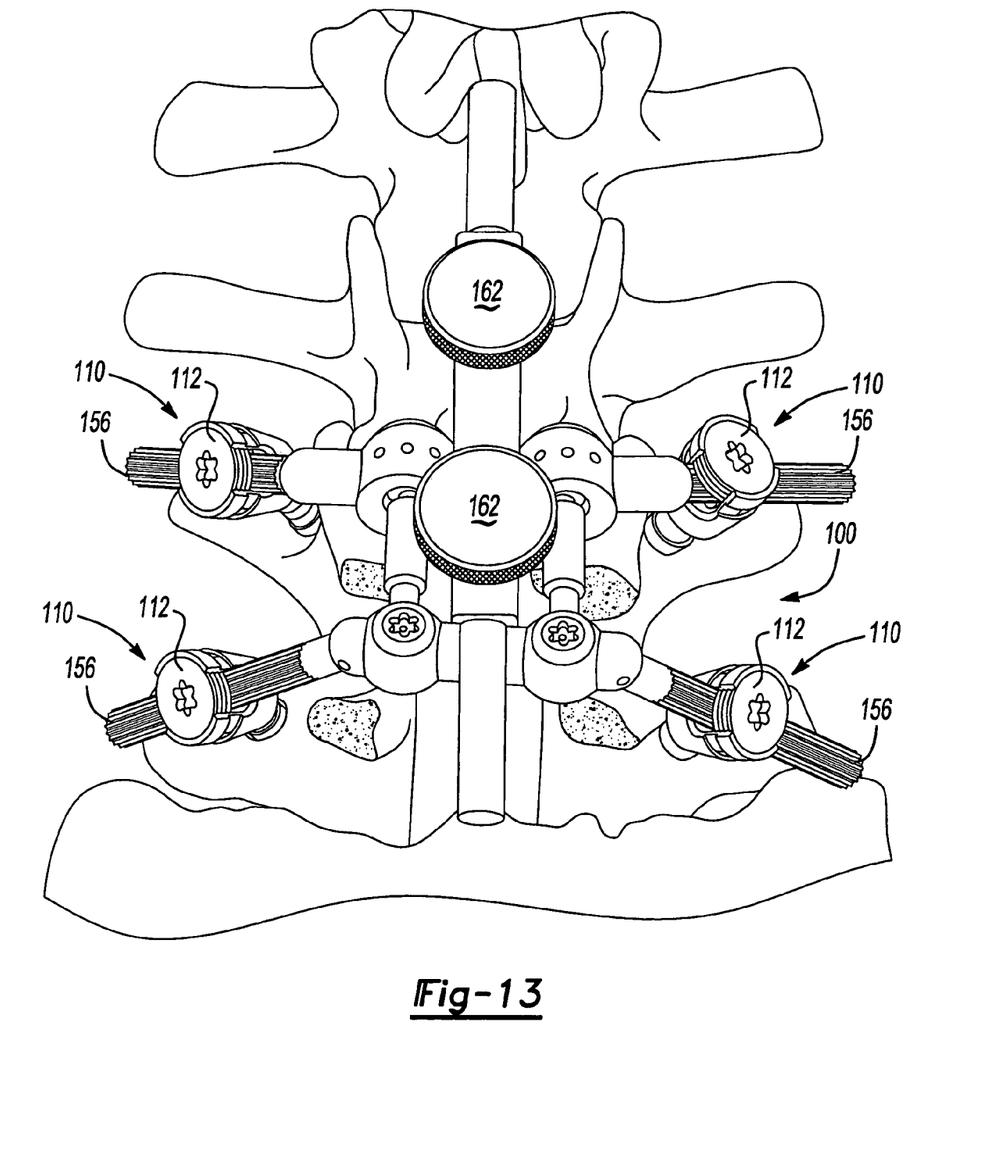

Referring to FIG. 13, the set screws 112 are tightened with a torque wrench or other tool to hold the arms 156 in a desired orientation. The assembly holder 160 is removed after disengaging the fasteners 162 from the openings 158. The spinal fixation device 100 can be used in the configuration shown in FIG. 2, in which the telescoping assemblies 128 allow relative motion between the first and second arm assemblies 124, 126 for dynamic spine motion, while limiting compression of the spine. Alternatively, the relative motion of the telescopic assemblies 128 can be constrained temporarily or permanently at a selected relative position of the first and second shafts 130, 132 by using, for example, suitable clamps, crimping or other known locking devices, thereby allowing the surgeon to adjust the amount of compression permitted and to constraint the spine in a desired configuration.

Figure 14:
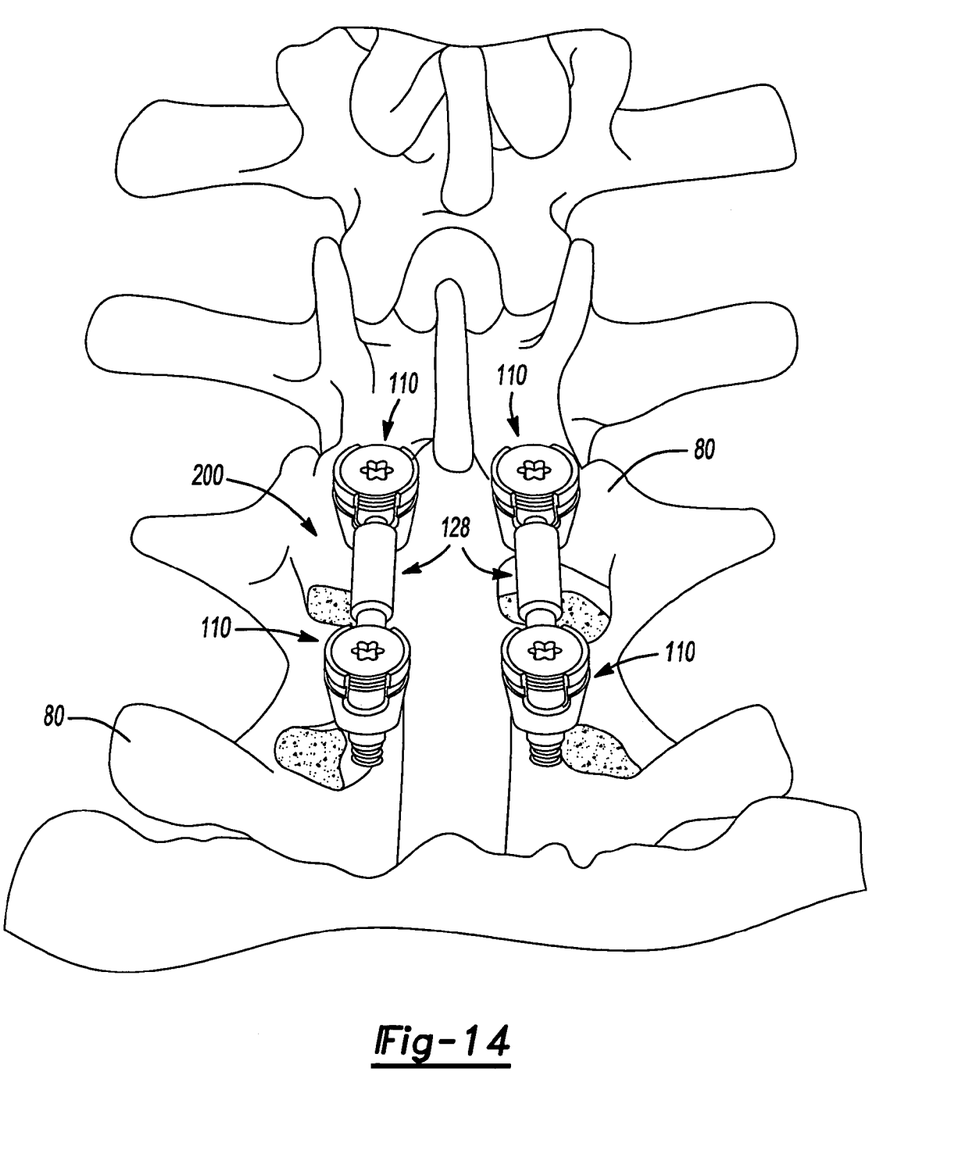
FIG. 14 is a perspective view of a spinal fixation device according to the present teachings, the spinal fixation device shown coupled to two vertebrae.

Referring to FIG. 14, another exemplary fixation device 200 according to the present teachings is illustrated attached to two vertebrae 80 of the posterior spine. As shown, the spinal fixation device 200 may be attached to the pedicles of the two vertebrae 80 with four multidirectional pedicle fasteners 110. In this embodiment, the vertebrae 80 are constrained in relative extension and compression by telescopic assemblies 128 which couple adjacent pedicle fasteners 110 of adjacent vertebrae 80. Although four pedicle fasteners 110 coupled with two telescopic assemblies are illustrated in FIG. 14, it will be appreciated that a plurality of adjacent vertebrae can be constrained in similar manner using additional pedicle fasteners 110 and telescopic assemblies 128.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A spinal fixation device comprising:
   a first arm assembly including a central portion and first and second arms extending from the central portion, the first and second arms attachable to corresponding first and second pedicles of a first vertebra of a spine, the first arm assembly extendable between the first and second pedicles of the first vertebra;
   a second arm assembly including a central portion and first and second arms extending from the central portion, the first and second arms attachable to corresponding first and second pedicles of a second vertebra, the second arm assembly extendable between the first and second pedicles of the second vertebra; and
   at least one telescopic assembly of variable length movably interconnecting the central portions of the first and second arm assemblies for relative motion therebetween, the telescopic assembly oriented substantially transversely to the central portions of the first and second arm assemblies, wherein each of the central portions of the first and second arm assemblies defines at least one integrally formed curved receiver portion for receiving respective ends of the at least one telescopic assembly.

2. The spinal fixation assembly of claim 1, wherein the telescopic assembly is sized for variable spinal compression between the first and second vertebrae along the spine direction up to a maximum predetermined amount of motion.

3. The spinal fixation assembly of claim 1, wherein the telescopic assembly can be adjustably constrained for variable spinal compression up to a predetermined amount.

4. The spinal fixation assembly of claim 1, wherein the telescopic assembly is coupled to the receiver portion of the first arm assembly for multiplanar directional movement and to the receiver portion of the second arm assembly for planar directional movement.

5. The spinal fixation assembly of claim 1, wherein the telescopic assembly includes first and second shafts telescopically interconnected.

6. The spinal fixation assembly of claim 5, wherein the first shaft includes a ball head rotatably received in the receiver portion of the central portion of the first arm assembly.

7. The spinal fixation assembly of claim 5, wherein the second shaft includes a ball portion rotatably received in the receiver portion of the central portion of the second arm assembly.

8. The spinal fixation assembly of claim 5, wherein the first and second shafts include engagement formations for variable spinal extension up to a maximum predetermined amount.

9. The spinal fixation assembly of claim 1, wherein each arm assembly includes a pair of pedicle fasteners for attaching each arm assembly to the corresponding vertebra.

10. The spinal fixation assembly of claim 9 wherein the pedicle fasteners are multi-directional.

11. The spinal fixation assembly of claim 9 further comprising a pair of set screws coupled to the pedicle fasteners for securing the arms to the corresponding pedicle fasteners, the set screws having ridge formations engaging complementary ridge formations of the arms.

12. The spinal fixation assembly of claim 11, in combination with removable guides for retaining the spinal fixation device onto the pedicle fasteners and engaging the set screws.

13. The spinal fixation assembly of claim 1, wherein the arms are angled relative to the central portion.

14. The spinal fixation assembly of claim 1, in combination with a removable arm holder for constraining telescopic movement of the at least one telescopic assembly during implantation.

15. The spinal fixation assembly of claim 1, wherein the telescopic assembly is configured for variable spinal extension.

16. A spinal fixation device comprising a plurality of arm assemblies, each arm assembly attachable to a corresponding vertebra, wherein pairs of adjacent arm assemblies are movably coupled to one another by one or more telescopic assemblies oriented substantially transversely to the vertebrae, each telescopic assembly having variable length and allowing relative movement between adjacent vertebrae.

17. The spinal fixation assembly of claim 16, wherein each telescopic assembly comprises first and second shafts telescopically coupled.

18. The spinal fixation assembly of claim 17, wherein the first shaft includes a ball head received in an integrally formed receiver portion of a first arm assembly of the plurality of arm assemblies and is rotatably and angulatably coupled to the first arm assembly.

19. The spinal fixation assembly of claim 17, wherein the second shaft includes a ball received in an integrally formed receiver portion of a second arm assembly of the plurality of arm assemblies and is coupled to the second arm assembly for planar angulation.

20. The spinal fixation assembly of claim 17, wherein the first and second shafts are configured for variable spinal extension and variable spinal compression up to maximum predetermined amounts.

21. The spinal fixation assembly of claim 16, in combination with multidirectional pedicle fasteners.

22. A method for spinal fixation comprising:
   providing a spinal fixation device comprising first and second arm assemblies transversely interconnected with one or more telescopic assemblies of variable length for relative movement therebetween;
   constraining relative movement of the first and second arm assemblies of the spinal fixation device with an assembly holder;
   inserting first and second pairs of pedicle fasteners on corresponding first and second adjacent vertebrae;
   coupling the first arm assembly to the first vertebra and substantially transversely to the spine;
   coupling the second arm assembly to the second vertebra and substantially transversely to the spine;
   removing the assembly holder; and
   allowing telescopic movement of the one or more telescopic assemblies and corresponding relative movement between the first and second vertebrae.

23. The method of claim 22, further comprising securing the first and second arm assemblies of the spinal fixation device on the pedicle fasteners with set screws.

24. The method of claim 23, wherein each of the first and second arm assemblies includes corresponding first and second pairs of arms, the method further comprising holding the first and second pairs of arms of the fixation device against the pedicle fasteners with removable guides.

25. The method of claim 24, further comprising engaging complementary ridge formations of the arms and the set screws.

26. A spinal fixation device comprising:
   first and second bone screws attachable to a first vertebra;
   third and fourth bone screws attachable to a second vertebra adjacent the first vertebra; and
   at least one telescopic assembly having variable length, the telescopic assembly movably coupling the first and third bone screws substantially transversely to the first and second vertebrae and allowing relative movement between the first and second vertebrae.

27. The spinal fixation device of claim 26, wherein each telescopic assembly comprises first and second shafts telescopically coupled.

28. The spinal fixation device of claim 27, wherein the first and second shafts are configured for variable spinal extension and variable compression to maximum predetermined amounts.

* * * * *

UNITED STATES PATENT AND TRADEMARK OFFICE
CERTIFICATE OF CORRECTION

PATENT NO. : 7,294,129 B2  Page 1 of 1
APPLICATION NO. : 11/062330
DATED : November 13, 2007
INVENTOR(S) : Nathaniel E. Hawkins et al.

It is certified that error appears in the above-identified patent and that said Letters Patent is hereby corrected as shown below:

Title Page
Item [57] Abstract, insert --be-- after "The telescopic assemblies can"

Column 2
Line 54, "1.28" should be --128--

Column 4
Line 59, "constraint" should be --constrained--

Signed and Sealed this

Fifteenth Day of April, 2008

JON W. DUDAS
*Director of the United States Patent and Trademark Office*